(12) United States Patent
Dane et al.

(10) Patent No.: US 9,078,944 B2
(45) Date of Patent: Jul. 14, 2015

(54) SYSTEM AND METHOD OF LABELING AND IDENTIFYING THE CONTENTS WITHIN A STERILIZATION CASE

(75) Inventors: Gary T. Dane, Bow, NH (US); Kraig Herman Allen, N. Leesburg, IN (US)

(73) Assignee: Symmetry Medical Manufacturing, Inc., Warsaw, IN (US)

( * ) Notice: Subject to any disclaimer, the term of this patent is extended or adjusted under 35 U.S.C. 154(b) by 1026 days.

(21) Appl. No.: 12/752,500

(22) Filed: Apr. 1, 2010

(65) Prior Publication Data
US 2010/0252473 A1 Oct. 7, 2010

Related U.S. Application Data

(60) Provisional application No. 61/165,557, filed on Apr. 1, 2009.

(51) Int. Cl.
| | |
|---|---|
| *B65D 85/00* | (2006.01) |
| *G09F 3/16* | (2006.01) |
| *G09F 3/08* | (2006.01) |
| *G09F 3/20* | (2006.01) |
| *B65B 61/00* | (2006.01) |
| *A61L 2/26* | (2006.01) |
| *A61B 19/02* | (2006.01) |
| *G09F 3/00* | (2006.01) |
| *A61B 19/00* | (2006.01) |

(52) U.S. Cl.
CPC . *A61L 2/26* (2013.01); *A61B 19/02* (2013.01); *A61B 2019/446* (2013.01); *A61L 2202/182* (2013.01); *A61L 2202/24* (2013.01); *G09F 3/0298* (2013.01)

(58) Field of Classification Search
CPC .. A61B 19/02; A61B 19/026; A61B 19/0201; A61B 19/0202; A61B 19/0219; B65D 55/02; B42F 5/06; B42F 5/00; G09F 3/0297; G09F 3/02; G09F 2003/0208
USPC .................. 206/828, 459.1, 459.5, 831, 447; 40/312, 594, 310, 778, 773
See application file for complete search history.

(56) References Cited

U.S. PATENT DOCUMENTS

| | | | | |
|---|---|---|---|---|
| 1,863,430 | A * | 6/1932 | Woerner, Jr. .................... | 40/778 |
| 2,335,793 | A * | 11/1943 | Ruppin ........................ | 40/778 |
| 3,125,460 | A * | 3/1964 | Rose .............................. | 428/194 |
| 4,268,000 | A * | 5/1981 | Ulm .............................. | 248/467 |
| 5,089,337 | A * | 2/1992 | Hochfeld ....................... | 428/352 |
| 5,732,821 | A | 3/1998 | Stone et al. | |
| 6,173,837 | B1 * | 1/2001 | Marconi ....................... | 206/457 |
| 6,793,075 | B1 * | 9/2004 | Jeter ........................... | 206/459.1 |
| 7,341,148 | B2 * | 3/2008 | Bettenhausen et al. ....... | 206/370 |
| 7,806,257 | B2 * | 10/2010 | Samaras et al. ................ | 206/150 |
| 2004/0031179 | A1 * | 2/2004 | Cumberland ................... | 40/778 |
| 2005/0016879 | A1 * | 1/2005 | Frederiksen ................. | 206/312 |
| 2007/0095699 | A1 | 5/2007 | Frieze et al. | |

* cited by examiner

*Primary Examiner* — Andrew Perreault
(74) *Attorney, Agent, or Firm* — Hayes Soloway PC

(57) ABSTRACT

The system contains at least two elongated feet attached to a wall of the sterilization case. Each of the feet is approximately parallel to the wall of the sterilization case and attached to the wall. At least one leg is integral with the each of the elongated feet. At least one retaining element extends from each of the legs.

2 Claims, 5 Drawing Sheets

SYSTEM AND METHOD OF LABELING AND IDENTIFYING THE CONTENTS WITHIN A STERILIZATION CASE

CROSS REFERENCE TO RELATED APPLICATION

This application claims benefit of U.S. Provisional Application Ser. No. 61/165,557 filed Apr. 1, 2009, the entire disclosure of which is incorporated herein by reference.

FIELD

The present disclosure is generally related to sterilization cases, and more particularly is related to a system and method for labeling and identifying the contents within a sterilization case.

BACKGROUND

Sterilization cases are utilized for sterilizing medical instruments. The sterilization cases retain the medical instruments and are inserted into a sterilizing machine, which sterilizes the medical instruments through a filter and openings formed in the sterilization cases. The sterilization cases may then continue to house the medical instruments until the medical instruments are needed, providing the container is not opened and/or the seal of the container is not compromised so that the contents remain sterile. However, with the openings formed in the sterilization cases, storage over a significant period of time may cause the medical instruments to become unsanitary with dust. Also, for record keeping purposes, it may be useful to keep records with the sterilization cases that include information related to the contents and can inform someone handling the sterilization cases when the medical instruments contained therein were last sterilized and verification that the instruments have, in fact, been sterilized. Standard sterilization cases are not built for record-keeping, leaving records to adhesively attached notes on the cases after sterilization is complete.

Thus, a heretofore unaddressed need exists in the industry to address the aforementioned deficiencies and inadequacies.

SUMMARY

Embodiments of the present disclosure provide a system and method for labeling a sterilization case. Briefly described, in architecture, one embodiment of the system, among others, can be implemented as follows. The system contains at least two elongated feet attached to a wall of the sterilization case. Each of the feet is approximately parallel to the wall of the sterilization case and attached to the wall. At least one leg is integral with the each of the elongated feet. At least one retaining element extends from each of the legs.

Briefly described, in architecture, a second embodiment of the system can be implemented as follows. A medical sterilization case has at least one wall. A plurality of elongated feet are attached to the wall, wherein one of the plurality of elongated feet is attached to the wall at a first position and another of the plurality of elongated feet is attached to the wall at a second position, different from the first position. At least one leg is connected to each of the plurality of elongated feet and rising away from the wall. At least one retaining element is connected to and extending from each of the legs, wherein an interior surface of the retaining element is located proximate to an exterior surface of the wall thereby forming a open gap. At least one labeling element has at least one labeling face. The labeling element is removably housed within the open gap, wherein at least a portion of the retaining element covers at least a portion of the labeling face.

The present disclosure can also be viewed as providing a method of labeling and identifying the contents within a sterilization case without compromising a sterile field of the sterilization case. In this regard, one embodiment of such a method, among others, can be broadly summarized by the following steps: attaching at least two elongated feet to a wall of the sterilization case, each of the elongated feet approximately parallel to the wall of the sterilization case; affixing at least one leg integral with each of the elongated feet; and forming at least one retaining element extending from each of the legs.

Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims.

BRIEF DESCRIPTION OF THE DRAWINGS

Many aspects of the disclosure can be better understood with reference to the following drawings. The components in the drawings are not necessarily to scale. Instead emphasis is being placed upon illustrating clearly the principles of the present disclosure. Moreover, in the drawings, like reference numerals designate corresponding parts throughout the several views.

DETAILED DESCRIPTION

Figure 1:
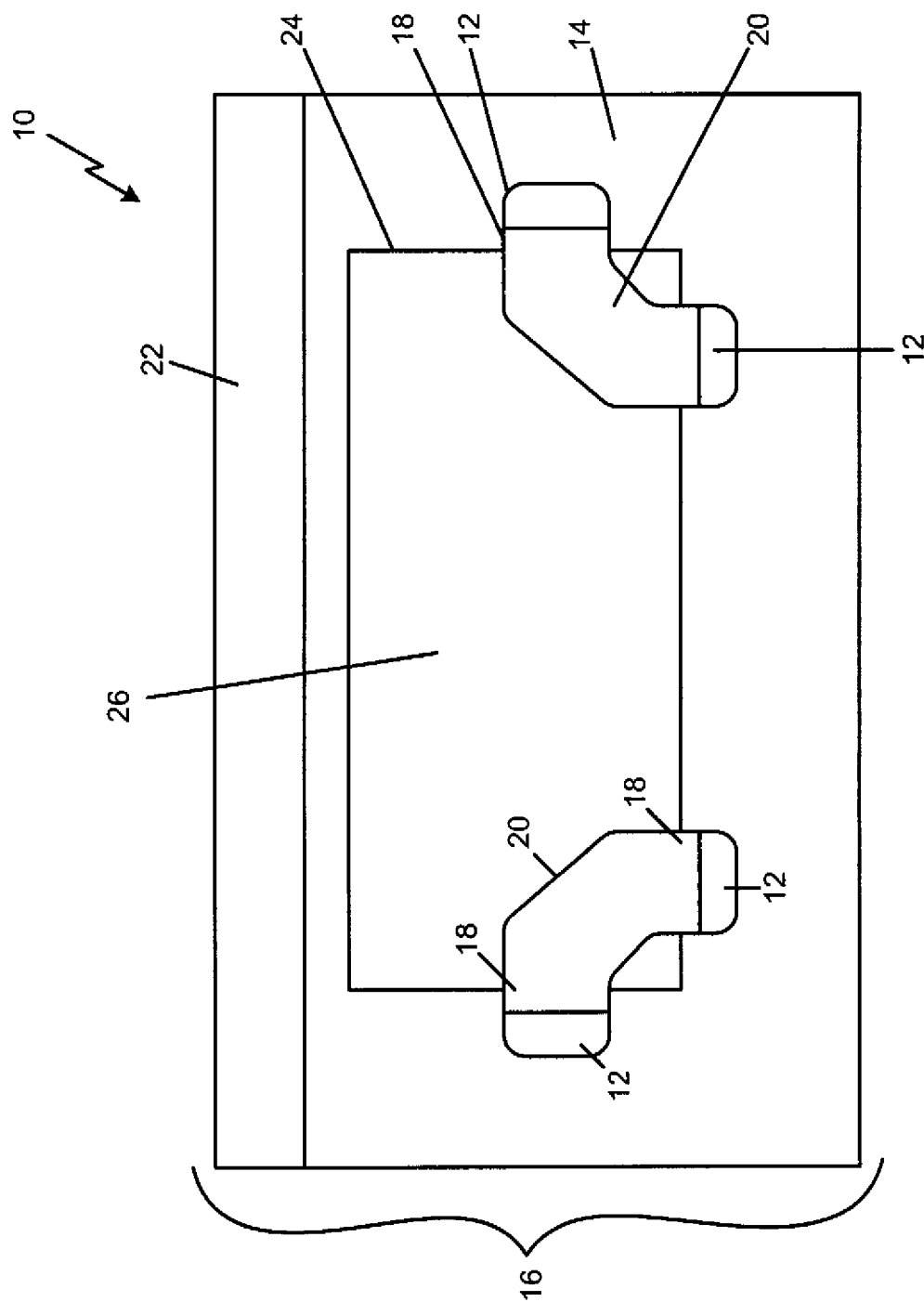
FIG. 1 is an illustration of a front view of a sterilization case labeling system, in accordance with a first exemplary embodiment of the present disclosure.

FIG. 1 is an illustration of a front view of a system 10 for labeling and identifying the contents within a sterilization case 16, in accordance with a first exemplary embodiment of the present disclosure. The system 10 is capable of labeling and identifying the contents within a sterilization case 16 without compromising the sterile field of the sterilization case 16. The system 10 contains at least two elongated feet 12 attached to a wall 14 of the sterilization case 16. Each of the feet 12 is approximately parallel to the wall 14 of the sterilization case 16. At least one leg 18 is integral with the each of the elongated feet 12. At least one retaining element 20 extends from each of the legs 18.

The system 10 is intended for use with any type of sterilization case 16, commonly one that includes a plurality of walls 14 and a cover 22. As illustrated in this embodiment, the system 10 may attach to one of the walls 14, although a similar system utilized on a cover 22 of the sterilization case 16 is within the scope of the present disclosure. The sterilization case 16 may include any shape, size or design, and will generally be a cuboidal in design, wherein at least one of the six sides is the cover 22. The sterilization case 16 will commonly have planar walls 14 but may include walls 14 with slight non-planar variations, such as walls 14 with arcs or bends, or walls 14 that have chamfered corners, perforations or other textural features.

The system 10 includes at least two elongated feet 12, and will commonly have four feet 12 or any additional number of feet 12. Any number or portion of the feet 12 may include a variety of designs that allow the system 10 to have a wide range of uses. For example, as is shown in FIG. 1, the system 10 may include four feet 12 configured on opposing ends of the wall 14. Commonly, at least one of the feet 12 will be attached to the wall 14 at a first position and another foot 12 will be attached to the wall 14 at a second position different from the first position. Other variations, designs and configurations may also be employed to improve the aesthetic quality, efficiency, convenience or ease of use of the system 10, all of which are considered within the scope of the present disclosure.

The feet 12 may be attached to the wall 14 with an adhesive material, such as an adhesive that is biologically safe and is resilient in a sterilizing environment. In addition, the feet 12 may be mechanically attached to the wall 14 with any number of mechanical fasteners or attachment techniques. This may include threaded fasteners, biased fasteners, removable and non-removable fasteners, welding attachment techniques, such as those commonly used with metals and thermoplastics. Accordingly, attaching the feet 12 to the wall 14 may also include addition aspects, such as cleaning a surface of the feet 12 or wall 14, a heat treatment or another treatment to create or enhance an attachment. Other devices have been utilized to mechanically attach materials to parts of a sterilization case and all such mechanical means are considered to be within the scope of the present disclosure.

Integral with the feet 12 is at least one leg 18. In FIG. 1, each of the two sets of feet 12 has an integral leg 18. The leg 18 may be characterized as any structure that connects at least one of the two feet 12 with a retaining element 20. Commonly, the leg 18 will rise away from the wall 14, whereby a gap is created behind a connected retaining element 20. The gap, discussed more with respect to FIG. 2, may be any size such that a labeling material 24 may be placed within the retaining element 20.

The at least one retaining element 20 is connected to and extends from the leg 18 and retains a labeling material 24 proximate to the wall 14. Any number of retaining elements 20 may be used with the system 10. Likewise, a variety of different configurations and designs may be used with the retaining element, such as a solid retaining structure extending between two legs 18, as is shown in FIG. 1. The retaining element 20 may also be a non-solid material such as a perforated or mesh material. Similarly, the retaining element 20 may include variations to enhance use of the system 10, such as a see-through design whereby labeling material 24 may be more easily visible a user of the system 10. The retaining element 20 may also include features designed to secure the labeling element 24 between the retaining element 20 and the wall 14 of the sterilization case 20. This may include textual components like rubber coatings or features to retain a labeling element 24 in place.

The labeling material 24 may have at least one labeling face 26 and may be placed within the retaining elements 20 and proximate to the wall 14 of the sterilization container 16. As is shown in FIG. 1, this may include placing one or more corners of the labeling material 24, or another portion of the labeling material 24 within the retaining elements 20. When in use, the labeling material 24 may be located between the at least two elongated feet 12 that are attached to the wall 14. The labeling material 24 and/or the labeling face 26 may be used to identify the recent history of the instruments contained in the sterilization case 16, such as the dates and times when medical instruments were utilized and sterilized. The labeling material 24 may also contain other information relating to the instruments contained in the sterilization case 16, such as sterilization status, type and quantity of instruments contained, personnel associated with a sterilizing process and/or any additional information commonly associated with sterilization of medical instruments.

The labeling material 24 may be constructed from a variety of materials having a number of designs, such as paper-based index cards, laminated cards, dry erase boards, or any other material that may be useful for labeling. The labeling material 24 may or may not be sufficiently resilient to enter a sterilization environment or endure a sterilizing process, depending on design and use. For example, if the labeling material 24 is an index card, it may deteriorate if it is placed within a sterilizing environment, such as an autoclave, which may have a sterilization environment with high temperatures, liquids and pressures. However, the labeling material 24 may be constructed of materials that can withstand a sterilization process, such as metals, plastics and compositions of resilient materials. The labeling material 24 may be interchangeable, preprinted tiles representing dates of cleaning, usage, or the like. It is preferable that a labeling material 24 is kept proximate to the sterilization case 16 at substantially all times, even during the exposure to the autoclave, although a labeling material 24 may be removed from the sterilization case 16 at any time.

The system 10 may also include a coding system, such that labeling material 24 can be removed from the sterilization cases 16 during sterilization and then matched back with the sterilization cases 16 after they exit the sterilization machines. This may include a color-coding system or an ascribe coding system, which matches an element of the system 10 and to the labeling material 24. Accordingly, a coding element 30 may be located on at least one of the elongated feet 12, the leg 18, the retaining element 20 and any retaining bar (FIGS. 3-4) whereas a second and corresponding coding element 32 may be located on the labeling material 24. Within this disclosure, ascribe coding may include any form of textual, numerical or symbol-based coding that helps identify a labeling material 24 with a sterilization case 16, a characteristic of the sterilization case 16, such as sterilized or non-sterilized, or a characteristic of an instrument within the sterilization case. Labeling material 24 may also be durable, preprinted material containing the coding element while in the autoclave, then switched with a less durable matched labeling material 24 after completing sterilization.

In accordance with the first exemplary embodiment, the system 10 may include any number of feet 12, legs 18, and retaining elements 20 in any combination. The feet 12, legs 18, and retaining elements 20 within the system 10 may be provided as a unitary element, such as a single structure, may be formed separately and assembled, or any combination thereof. Additionally, while only the two sets of feet 12, legs 18, and retaining elements 20 are shown in FIG. 1 at an underside of the labeling material 24, such that gravity may aid in retaining the labeling material 24, the two sets of feet 12, legs 18, and retaining elements 20 may be placed at opposing corners of the labeling material 24 and/or may frictionally retain the labeling material without utilizing gravity. Other designs and configurations may also be employed, as would be recognized by one having ordinary skill in the art, all of which are considered within the scope of the present disclosure.

Figure 2:
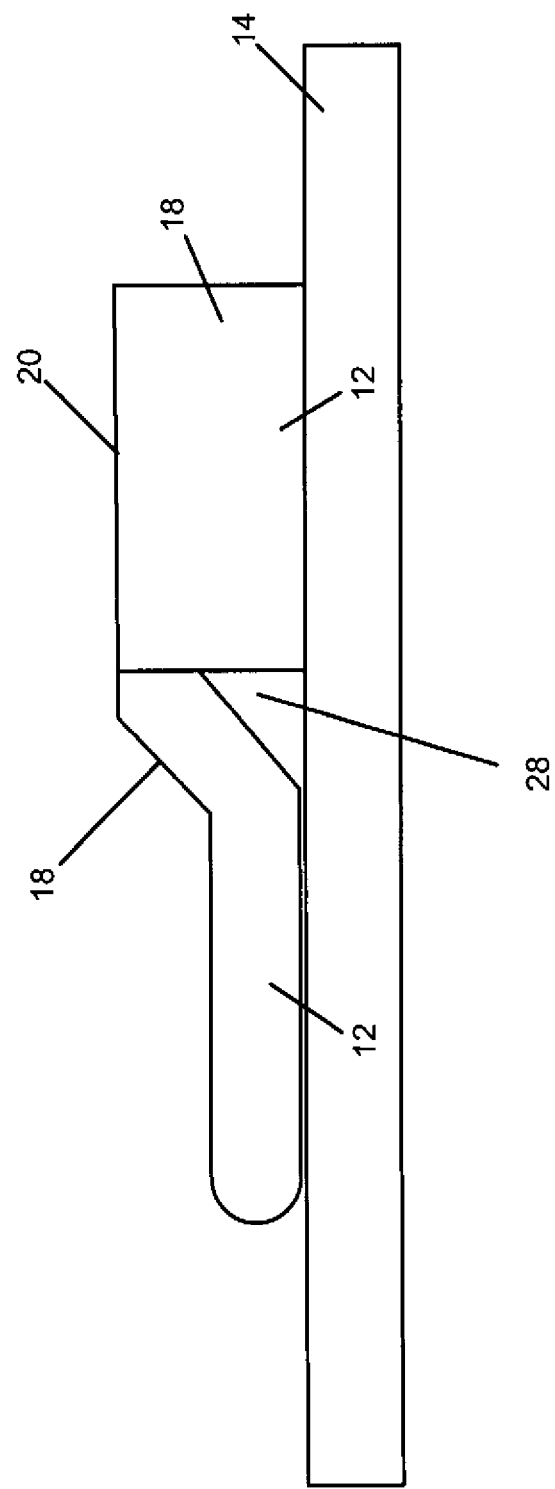
FIG. 2 is an illustration of a side view of a portion of the sterilization case labeling system of FIG. 1, in accordance with the first exemplary embodiment of the present disclosure.

FIG. 2 is an illustration of a side view of a portion of the system 10 for labeling and identifying the contents within a sterilization case 16 of FIG. 1, in accordance with the first exemplary embodiment of the present disclosure. The side view illustration includes two feet 12, two legs 18, and one retaining element 20 along with a portion of the wall 14. As can be seen, the feet 12 are oriented parallel to the wall 14. This may allow for a durable attachment between the feet 12 and the wall 14. FIG. 2 also better illustrates the position of the legs 18 rising away from the feet 12 and connected between the feet 12 and the retaining element 20.

FIG. 2 also provides a detailed illustration of the gap 28 that is formed between the interior surface of the retaining element 20 and the exterior surface of the wall 14. The gap 28 may also be referred to as an open gap, may include any size, and will commonly have a size such that the system 10 easily houses labeling material 24. Accordingly, the labeling material 24 may be removably housed with the gap 28, whereby at least a portion of the retaining element 20 covers at least a portion of the labeling face 26 of the labeling material 24.

Figure 3:
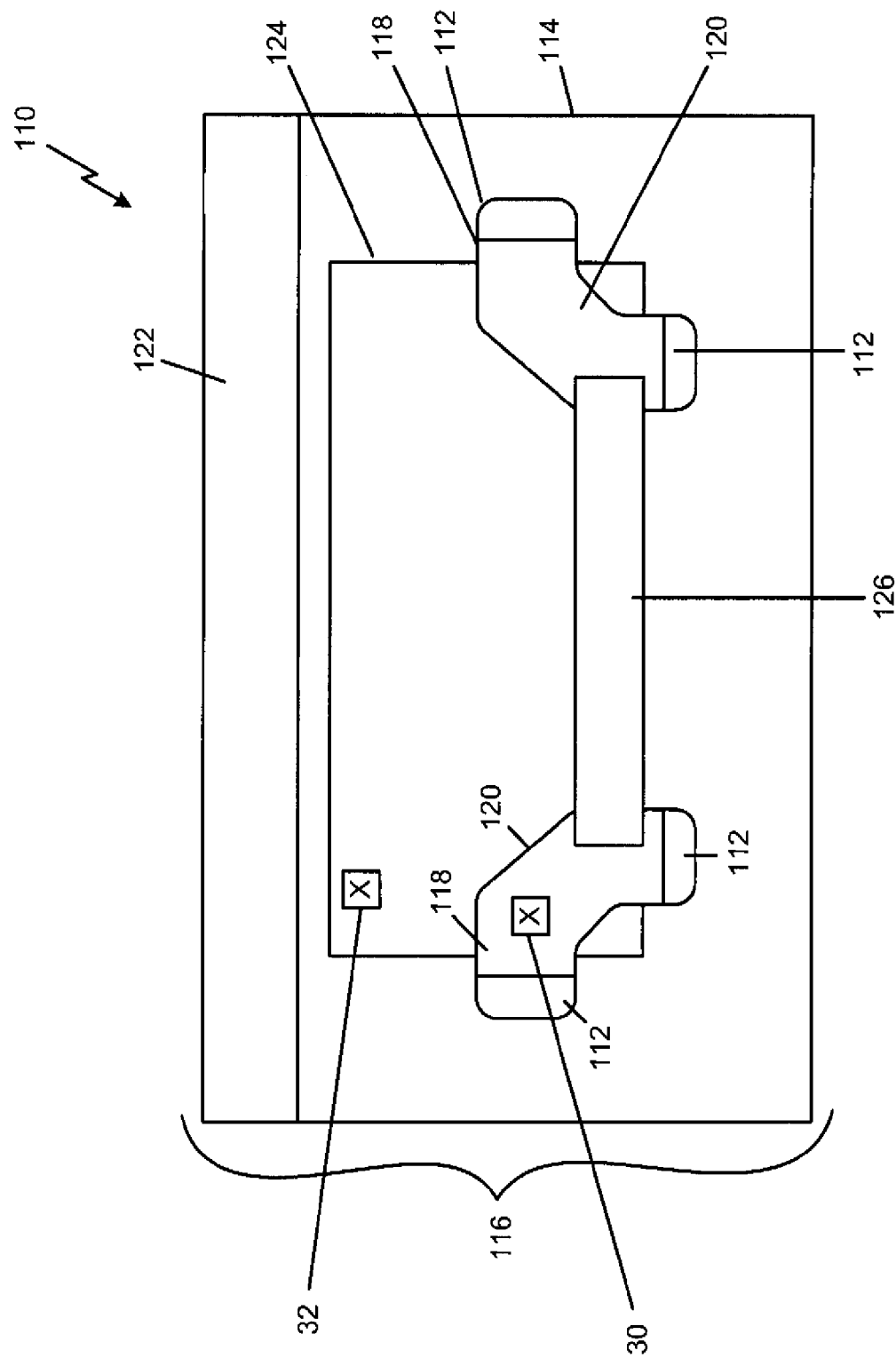
FIG. 3 is an illustration of a prospective view of a sterilization case labeling system, in accordance with a second exemplary embodiment of the present disclosure.

FIG. 3 is an illustration of a prospective view of a system 110 for labeling and identifying the contents within a sterilization case 116, in accordance with a second exemplary embodiment of the present disclosure. The system 110 may be similar to the system 10 of the first exemplary embodiment, and therefore may contain similar features and designs. The system 110 contains at least two elongated feet 112 attached to a wall 114 of the sterilization case 116. Each of the feet 112 is approximately parallel to the wall 114 of the sterilization case 116 and attached to the wall 114. At least one leg 118 is integral with the each of the elongated feet 112. At least one retaining element 120 extends from each of the legs 118.

The system 110 includes a retaining bar 126 extending between the retaining elements 120. Any number of retaining bars may be used with the system 110. The retaining bar 126 may be provided with the retaining elements 120 or it may be formed separately and attached thereto. The retaining bar 126 may be useful for retaining the labeling material 124, particularly if the labeling material 124 is flimsy and does not easily stay in a position proximate to the wall 114 of the sterilization case 116 or comprises a plurality of independent elements. The retaining bar 126 may be planar or may have a non-planar design, such as an L-shaped cross-section with a tab extends from the retaining bar 126 toward the wall 114. The retaining bar 126 is generally independent of the wall 114, but it may be connected to or in contact with the wall 114 of the sterilization case 116.

Figure 4:
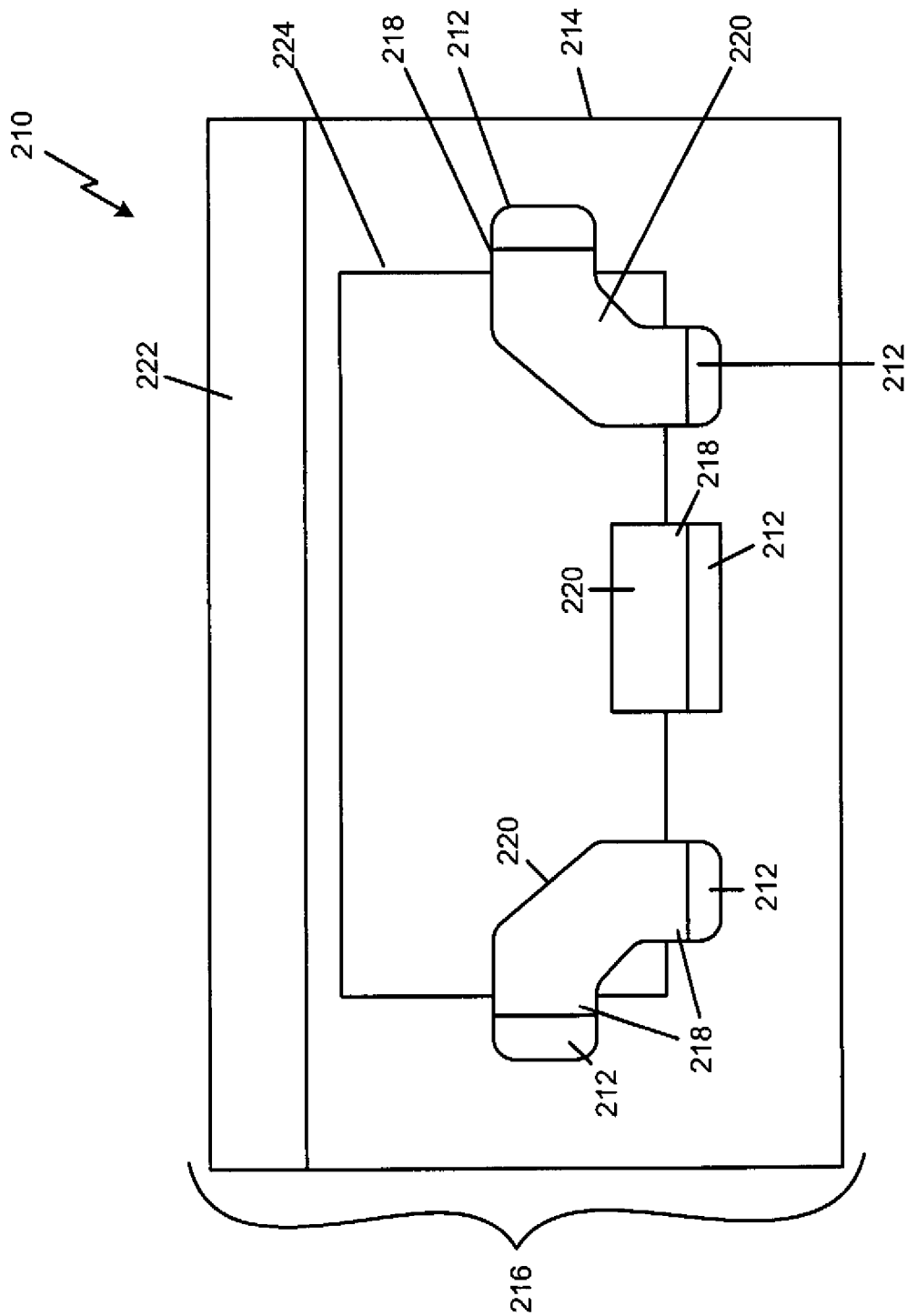
FIG. 4 is an illustration of a prospective view of a sterilization case labeling system, in accordance with a third exemplary embodiment of the present disclosure.

FIG. 4 is an illustration of a prospective view of a system 210 for labeling and identifying the contents within a sterilization case 216, in accordance with a third exemplary embodiment of the present disclosure. The system 210 may be similar to the system 10 of the first exemplary embodiment and the system 110 of the second exemplary embodiment, and therefore may contain similar features and designs. The system 210 contains at least two elongated feet 212 attached to a wall 214 of the sterilization case 216. Each of the feet 212 is approximately parallel to the wall 214 of the sterilization case 216 and attached to the wall 214. At least one leg 218 is integral with the each of the elongated feet 212. At least one retaining element 220 extends from each of the legs 218.

The third exemplary embodiment includes three retaining elements 220, five legs 218, and five feet 212. As is shown in FIG. 4, the middle retaining element 220 is supported by only one leg 218 and one foot 212. While all three retaining elements 220 are shown mounted along a bottom edge of the labeling material 224, the middle retaining element 220 may be located along a top edge of the labeling material 224 without departing from the scope of the present disclosure. Also, the system 210 may be practiced with retaining elements 220 that each only has one leg 218 and one foot 212 without departing from the scope of the present disclosure. In such a practice, the retaining elements 220 may be aligned with a plurality of edges of the labeling material 224. Similar to the second exemplary embodiment, the third exemplary embodiment may include adding a retaining member between any of the retaining elements 220 to help secure a flimsy labeling material 224.

Figure 5:
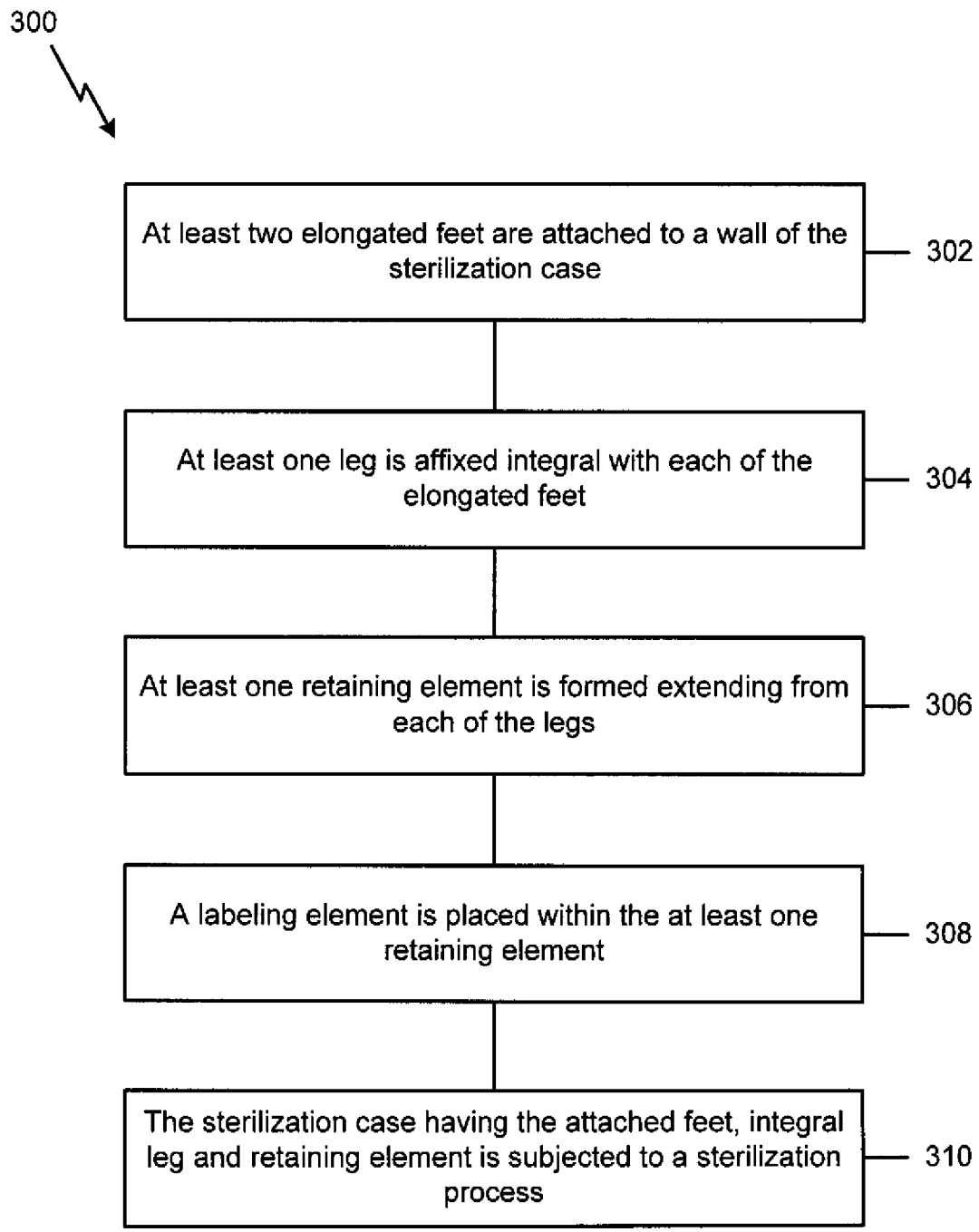
FIG. 5 is a flowchart illustrating a method of labeling and identifying the contents within a sterilization case of FIG. 1, in accordance with the first exemplary embodiment of the disclosure.

FIG. 5 is a flowchart 300 illustrating a method of labeling and identifying the contents within a sterilization case 16 of FIG. 1, in accordance with the first exemplary embodiment of the disclosure. It should be noted that any process descriptions or blocks in flow charts should be understood as representing modules, segments, portions of code, or steps that include one or more instructions for implementing specific logical functions in the process, and alternate implementations are included within the scope of the present disclosure in which functions may be executed out of order from that shown or discussed, including substantially concurrently or in reverse order, depending on the functionality involved, as would be understood by those reasonably skilled in the art of the present disclosure.

As is shown by block 302 at least two elongated feet are attached to a wall of the sterilization case. Each of the elongated feet is positioned approximately parallel to the wall of the sterilization case. At least one leg is affixed integral with each of the elongated feet (block 304). At least one retaining element is formed extending from each of the legs (block 306). A labeling element is placed within the at least one retaining element (block 308). The sterilization case having the attached feet, integral leg and retaining element is subjected to a sterilization process (block 310). Additional steps and features may also be included with the method, and will vary by design and application. For example, the step of housing at least one labeling element between the wall of the sterilization case and the at least one retaining element may be included. Additionally, the step of removing the labeling element from the at least one retaining element and/or the step of subjecting the labeling element to the sterilization process may be included.

It should be emphasized that the above-described embodiments of the present disclosure, particularly, any "preferred" embodiments, are merely possible examples of implementations, merely set forth for a clear understanding of the principles of the disclosed system and method. Many variations and modifications may be made to the above-described embodiments of the disclosure without departing substantially from the spirit and principles of the disclosure. All such modifications and variations are intended to be included herein within the scope of this disclosure and protected by the following claims.

What is claimed is:

1. A system, with a sterilization case, for labeling and identifying contents within the sterilization case without compromising a sterile field of the sterilization case, the system comprising:

the sterilization case;

a cover and a plurality of walls forming the sterilization case;

at least two elongated feet attached to at least one wall of the plurality of walls of the sterilization case, each of the elongated feet approximately parallel to the at least one wall of the plurality of walls;

at least one leg integral with each of the elongated feet;

at least one retaining element extending from each of the legs;

at least one retaining element extending from each of the legs; at least one retaining bar between the at least two retaining elements; at least one labeling element between the at least one retaining bar and the at least one wall of the plurality of walls; and at least a first coding element on at least one of the elongated feet, the at least one leg, the at least one retaining element and the at least one retaining bar, wherein the first coding element corresponds to at least a second coding element on the at least one labeling element.

2. The system of claim 1, wherein the first and second coding elements further comprise at least one of color coding and ascribe coding.

\* \* \* \* \*